(12) United States Patent
Mlynash et al.

(10) Patent No.: US 6,615,075 B2
(45) Date of Patent: Sep. 2, 2003

(54) QRST SUBTRACTION USING AN ADAPTIVE TEMPLATE FOR ANALYSIS OF TU WAVE OBSCURED ATRIAL ACTIVITY

(75) Inventors: Michael D. Mlynash, Mountain View, CA (US); Arne Sippens Groenewegen, Burlingame, CA (US); Michael D. Lesh, Mill Valley, CA (US)

(73) Assignee: The Regents of the University of California, Oakland, CA (US)

(*) Notice: Subject to any disclaimer, the term of this patent is extended or adjusted under 35 U.S.C. 154(b) by 311 days.

(21) Appl. No.: 09/809,719

(22) Filed: Mar. 14, 2001

(65) Prior Publication Data

US 2001/0056245 A1 Dec. 27, 2001

Related U.S. Application Data

(60) Provisional application No. 60/196,204, filed on Apr. 11, 2000, provisional application No. 60/189,611, filed on Mar. 15, 2000, and provisional application No. 60/189,513, filed on Mar. 15, 2000.

(51) Int. Cl.$^7$ .............................................. A61B 5/0452
(52) U.S. Cl. ........................................ 600/513; 600/517
(58) Field of Search ................................ 600/508, 509, 600/513, 515, 516, 517, 518, 519; 705/2, 3

(56) References Cited

U.S. PATENT DOCUMENTS

| | | | | |
|---|---|---|---|---|
| 4,550,502 A | | 11/1985 | Grayzel ........................ 33/1 B |
| 4,721,114 A | | 1/1988 | DuFault et al. ............. 128/696 |
| 5,313,953 A | | 5/1994 | Yomtov et al. ............. 128/696 |
| 5,361,202 A | | 11/1994 | Doue .................... 364/413.01 |
| 5,377,687 A | | 1/1995 | Evans et al. ................ 128/700 |
| 5,447,519 A | * | 9/1995 | Peterson ..................... 600/518 |
| 5,609,158 A | | 3/1997 | Chan ........................... 128/705 |
| 5,652,842 A | | 7/1997 | Siegrist, Jr. et al. ........ 395/145 |
| 5,713,367 A | * | 2/1998 | Arnold et al. .............. 600/517 |
| 5,755,739 A | | 5/1998 | Sun et al. ...................... 607/14 |
| 5,772,604 A | | 6/1998 | Langberg et al. ........... 600/508 |
| 5,818,570 A | | 10/1998 | Urbanczyk .................... 355/75 |
| 5,840,038 A | | 11/1998 | Xue et al. .................... 600/512 |
| 6,038,476 A | | 3/2000 | Schwartz ...................... 607/27 |
| 6,064,906 A | | 5/2000 | Langberg et al. ........... 600/518 |
| 6,115,628 A | * | 9/2000 | Stadler et al. .............. 600/517 |
| 6,128,526 A | * | 10/2000 | Stadler et al. .............. 600/517 |

OTHER PUBLICATIONS

International Search Report Jun. 19, 2001.
Janet Slocum, Alan Sahakian, Steven Swiryn; "Diagnosis of atrial fibrillation from surface electrocardiograms based on computer-detected atrial activity;" Journal of Electrocardiology vol. 25 No. 1 Jan. 1992.
M. H. Sedaaghi; "ECG wave detection using morphological filters;" Applied Sig. Process (1998)5:182–194.

(List continued on next page.)

Primary Examiner—Willis R. Wolfe
(74) Attorney, Agent, or Firm—Lumen Intellectual Property Services, Inc.

(57) ABSTRACT

The present invention provides a noninvasive localization, characterization and classification apparatus and method for cardiac arrhythmias. The invention enables discrete isolation of the intricate spatial and temporal detail in morphology of the atrial activity of interest from superimposed ventricular activity of a preceding heartbeat in a particular arrhythmia. An adaptive QRST subtraction template is used that is modulated for discrepancies in voltage and rate between the QRST template and arrhythmia signal. The QRST template modulation is accomplished by using one or more fiducial points and windows that are annotated in both the QRST template and the arrhythmia signal. The invention includes, but is not limited to, the isolation of atrial activity that are commonly known as: (1) P waves in case of focal atrial fibrillation, atrial tachycardia, and orthodromic AV reentrant tachycardia; (2) fibrillation waves in case of chronic atrial fibrillation; and (3) flutter waves in case of atrial flutter.

74 Claims, 13 Drawing Sheets

OTHER PUBLICATIONS

C J Meurling, K Hnatkova, JEPWaktare, H Nagayoshi, T Janota, AJ Camm, M Malik; "Non–invasive assessment of atrial electrophysiology in AF–influence of posture change;" Computer in Cardlology 1998 vol. 25.

Magnus Holm, Steen Pehrson, Max Ingemansson, Leif Sornmo, Rolf Johansson, Lennart Sandhall, Max Sunemark, Birgit Smideberg, Christian Olsson, S. Bertil Olsson; "Non–invasive assessment of the atrial cycle length during atrial fibrillation in man: introducing, validating and illustrating;" Cardiovascular Research 38 (1998) 69–81.

Janet Slocum, Ernest Byrom, Lynn McCarthy, Alan Sahakian, Steven Swiryn; "Computer detection of atrioventricular dissociation from surface electrocardiograms during wide QRS complex tachycardias;" Diagnostic Methods Arrhythmia, vol. 72, No. 5, Nov. 1985.

Andreas Bollmann, Narendra K. Kanuru, Kevin K. McTeague, Paul F. Walter, David B. Delurgio, Jonathan J. Langberg; "Frequency analysis of human atrial fibrillation using the surface electrocardiogram and its response to ibutilide;" The American Journal of Cardiology vol. 81, Jun. 15, 1998.

Magnus Holm, Steen Pehrson, Max Ingemansson, Leif Sornmo, Rolf Johansson, Lennart Sandhall, Max Sunemark, Birgit Smideberg, Christian Olsson S. Bertil Olsson; "Non–invasive assessment of the atrial cycle length during atrial fibrillation in man: introducing, validating and illustrating a new ECG method;" Cardiovascular Research 38 (1998) 69–81.

Zhu Yi–Sheng, Nitish V. Thakor; P–wave detection by an adaptive QRS–T cancellation technique; 1987 IEEE.

M. Mlynash, A. Sippens Groenewegen, F. Roithinger, Y. Goseki, P. Steiner, M. Lesh; "Automated QRST subtraction algorithm for analysis of T wave obscured ectopic atrial beats;" Published in the proceeding of the 21th Annual Conference of the IEEE Engineering in Medicine and Biology Society, Oct. 13–16, 1999.

* cited by examiner

QRST SUBTRACTION USING AN ADAPTIVE TEMPLATE FOR ANALYSIS OF TU WAVE OBSCURED ATRIAL ACTIVITY

CROSS-REFERENCE TO RELATED APPLICATIONS

This application is based on provisional U.S. application No. 60/189,513 filed Mar. 15, 2000, provisional U.S. application No. 60/189,611 filed Mar. 15, 2000, provisional U.S. application No. 60/196,204 filed Apr. 11, 2000, all of which are herein incorporated by references. This application cross-references to U.S. non-provisional application Ser. No. 09/724,947 filed Nov. 28, 2000, which is herein incorporated by reference.

STATEMENT REGARDING FEDERALLY SPONSORED RESEARCH OR DEVELOPMENT

This invention was supported in part by grants from the National Institutes of Health HL09602 and R01-HL55027. The Government has certain rights in the invention.

FIELD OF THE INVENTION

This invention relates generally to electrocardiographic localization and classification of cardiac arrhythmias. More particularly, the present invention relates to noninvasive analysis of TU wave obscured atrial activity.

BACKGROUND ART

An arrhythmia is any deviation from or disturbance of the normal heart rhythm. This is when the heart's natural pacemaker develops an abnormal rate or rhythm (e.g. a tachycardia where the heart rate is faster than normal), the normal conduction pathway is interrupted, an abnormal or accessory conduction pathway controls the rhythm, or when another part of the heart takes over as an ectopic pacemaker. Arrhythmias may be benign, life threatening or even fatal depending on the type of arrhythmia. Several different types of arrhythmias can be distinguished, for example atrial tachycardia, atrioventricular (AV) node reentrant tachycardia, atrial fibrillation, atrial flutter, and ventricular tachycardia.

Although electrocardiographic arrhythmia evaluation is currently feasible by capturing spontaneous tachycardia episodes via ambulatory or emergency electrocardiogram (ECG) recording, analysis of the timing and presumed origin of atrial activation on the body surface is frequently hampered by the simultaneous occurrence of the higher voltage ventricular activation or recovery potentials. During both focal and incisional reentrant atrial tachycardia, the low-amplitude P wave (atrial activity) may be obscured by the preceding high-amplitude QRST segment (ventricular activity). Difficulties are encountered when visually assessing the P wave morphology of TU wave superimposed ectopic atrial beats that are critically related to atrial fibrillation triggered by a focal source, typically situated in one of the pulmonary veins. Similarly, localization of the atrial insertion site using the retrograde P wave morphology obtained during orthodromic AV reentrant tachycardia may be difficult due to partial or complete concealment by the TU wave.

The ability to completely isolate the P wave from a preceding cardiac cycle is particularly relevant with regard to recent reports describing the role of focal triggers in the initiation of atrial fibrillation (e.g. Haissaguerre, M. et al. (1998) *Spontaneous initiation of atrial fibrillation by ectopic beats originating in the pulmonary veins, N. Engl. J. Med.* 339:659–666). Localized adequately, these focal triggers are amenable to treatment and cure using radiofrequency catheter ablation. However, mapping of the premature beats that cause the initiation of atrial fibrillation using standard catheter techniques is cumbersome, lengthy, and unpredictable. Therefore, noninvasive electrocardiographic localization of these atrial premature beats before or during the invasive mapping procedure is highly preferable. However, since the P wave of these atrial premature beats is usually obscured by the preceding TU wave, application of a QRST subtraction algorithm to isolate and preserve the detailed P wave morphology is of critical importance to enable ECG-based trigger localization. However, to date no such algorithms exist that are capable of isolating and preserving the detailed P wave morphology.

So far, most people use QRST subtraction algorithms to detect P waves, fibrillation waves, or flutter waves by either a frequency analysis (e.g. U.S. Pat. No. 6,064,906), morphological filters (e.g. Sedaaghi, M. H. (1998), *ECG wave detection using morphological filters, Appl. Sign. Process.* 5:182–194), suppression and cross correlation techniques (e.g. U.S. Pat. No. 5,840,038), or an impulse correlated adaptive filter (e.g. Zhu Y. S. and Thakor N. V. P (1987), *P-wave detection by an adaptive QRST cancellation technique, In: Computers in Cardiology*; Eds. Ripley K. L., IEEE Comput. Soc. Press, Washington, D.C., pp. 249:252). A previously reported method on QRST algorithms employs additional measures to correct for rate-related differences in QRST duration (e.g. Slocum J. et al. (1992), *Diagnosis of atrial fibrillation from surface electrocardiograms based on computer-detected atrial activity, J. Electrocardiol.* 25:1–8). In addition, in previous reports and methods, the design of the QRST templates was done on the same data set that was subsequently subjected to QRST removal. In that case, the presence of AV dissociation was considered imperative to ensure that atrial activity would be preserved in the remaining signal after QRST subtraction.

Although, most of the before mentioned methods work well for P wave or fibrillation wave detection, they do not provide the ability to retain important spatial and temporal details regarding the specific morphology of the atrial activity. There is therefore a strong need for an improved clinical tool to achieve adequate isolation of TU wave superimposed atrial activity so that noninvasive electrocardiographic screening, localization and analysis of atrial arrhythmias can be carried out more effectively before or during an invasive electrophysiologic intervention.

OBJECTIVES AND ADVANTAGES

In light of the above, it is the primary objective of the present invention to provide an apparatus and method for electrocardiographically localizing and classifying atrial arrhythmias. More specifically, it is the objective of the present invention to provide a noninvasive apparatus and method for analysis of TU wave obscured atrial activity.

It is another objective of the present invention to provide an automatic QRST subtraction algorithm based on using an adaptive QRST template constructed from averaged QRST complexes combined with ECG recordings to enable discrete isolation of TU wave obscured ectopic atrial activity on the surface ECG while retaining the intricate spatial and temporal details in P wave morphology.

It is yet another objective of the present invention to obtain an optimal morphology subtraction performance in the TU wave range by correcting specifically for differences in both the QRST duration and voltage of the T wave.

It is still another objective of the present invention to provide a QRST template design based on a separate data set obtained during sinus rhythm and/or atrial pacing to ensure that atrial and ventricular activity are clearly separated.

It is still another objective of the present invention to provide for an optimal visualization of the P wave morphology in both supraventricular arrhythmias (i.e. atrial tachycardia and orthodromic AV reentrant tachycardia) and focal atrial ectopy where atrial activity coincides with ventricular recovery of the preceding cardiac cycle.

It is another objective of the present invention to isolate P waves from the superimposed TU wave during AV associated rhythms other than atrial ectopy (e.g. flutter waves in atrial flutter).

It is another objective of the present invention to isolate fibrillation waves during atrial fibrillation and to provide a clinical tool to achieve noninvasive localization of the triggers that initiate atrial fibrillation.

It is another objective of the present invention to enable the application of analyzing atrial arrhythmias, when atrial depolarization is obscured by the preceding ventricular repolarization.

It is another objective of the present invention to provide a tool that is used to develop and apply a database for classification of atrial arrhythmias.

The advantage of the present invention over the prior art is that it provides for a QRST subtraction algorithm based on using an adaptive QRST template while retaining the intricate spatial and temporal detail in atrial activity morphology, including P waves, fibrillation waves and flutter waves.

SUMMARY

The present invention provides an apparatus and method for localizing and classifying atrial arrhythmias. More specifically, the present invention provides a noninvasive apparatus and method for analysis of TU wave obscured atrial activity. The present invention includes an apparatus and method to isolate atrial activity wherein atrial activity is commonly known as, but not limited to: (1) a P wave in case of focal atrial fibrillation, atrial tachycardia, and orthodromic AV reentrant tachycardia; (2) a fibrillation wave in case of atrial fibrillation other than focal atrial fibrillation; and (3) a flutter wave in case of atrial flutter.

When localizing arrhythmia foci or the insertion site of an accessory pathway within an atrium, the atrial activity that is indicative of activity within the atrium, is often superimposed, either partially or completely, by the TU wave. Physiologically speaking, the atrial activity of interest may coincide with ventricular recovery of the preceding cardiac cycle. To accurately localize focal triggers of atrial fibrillation, atrial tachycardia, and accessory pathway insertion sites during orthodromic AV reentrant tachycardia, the present invention provides for a noninvasive arrhythmia localization and classification apparatus and method for effectively and optimally separating the atrial activity of interest from a superimposed preceding ventricular activity. More specifically, the present invention provides a QRST subtraction algorithm based on using an adaptive QRST template that enables discrete isolation of TU wave obscured ectopic atrial activity on the surface ECG while retaining the intricate spatial and temporal detail in atrial activity morphology.

Accordingly, the present invention provides a signal processor which is identified as the apparatus and method that performs the processing to generate a QRST template that is further adapted and ultimately used in QRST subtraction to output an isolated atrial activity, e.g. a P wave, a fibrillation wave, or a flutter wave. The signal processor receives the electrical heart signals indicative of a heart's atrial and ventricular activity obtained from the thoracic surface of a subject. After the QRST template is effectively subtracted from each measured signal containing an atrial activity of interest, the morphology of the isolated P wave, fibrillation wave, or flutter wave can be analyzed. Analysis parameters, such as for instance peak of the wave, duration of the wave, or multi-lead integral or potential map of the wave can be compared with a database containing a variety of analysis parameters of previously acquired P waves, fibrillation waves or flutter waves. The comparison with the database may then conclude on a localization or classification of a particular arrhythmia using noninvasive techniques upon which ablative treatment or another therapy decision would then be possible.

The present invention includes electrical heart signals that are acquired during sinus rhythm or atrial overdrive pacing. These electrical heart signals are used for the QRST template construction. For P wave and flutter wave isolation, the electrical heart signals that are used for QRST template construction have to be different from the electrical heart signal that is under investigation, i.e. the signal that is recorded during a particular arrhythmia (e.g. focal atrial fibrillation, atrial tachycardia, orthodromic AV reentrant tachycardia, or atrial flutter). Therefore, for P wave and flutter wave analysis, a clear distinction is made between the electrical heart signals obtained during an arrhythmia, called arrhythmia signals, and the electrical heart signals obtained during sinus rhythm or atrial pacing, called template signals that are used to create the QRST template. It is the arrhythmia signal that is eventually exposed to subtraction of the QRST template, after the template is adapted, to isolate the atrial activity that is obscured from the preceding heartbeat's ventricular activity. In case of fibrillation waves, the QRST template may also be designed from the electrical heart signal that is under investigation, i.e. the signal that is recorded during chronic atrial fibrillation.

The present invention includes sensors adapted to detect electrical heart signals. The sensors are distributed in an array across the thoracic skin of a subject. Generally, this employs a plurality of sensors distributed across the anterior and posterior skin surface of the torso of the subject, or to an alternative accessible body surface, for example via a transesophageal approach. However, the present invention enables the use of at least one sensor. Electrical heart signals from each sensor are preferably acquired simultaneously, amplified and converted into digital signals using an analog-to-digital converter. The present invention includes and is not limited to the transmission of electrical heart signals to the signal processor either by conventional electrical cables/wires or by wireless communication. Also the present invention is not limited to combinations of either conventional and wireless communication of the signals. This then enables remote detection, analysis, operation and treatment.

In accordance to exemplary embodiments, the signal processor receives at least two template signals that contain electrical heart signals obtained during sinus rhythm or atrial pacing for the construction of a QRST template. In addition, the signal processor receives an arrhythmia signal that contains electrical heart signals obtained during an actual arrhythmia and in which atrial activity is obscured by ventricular activity. In case of fibrillation wave isolation one may use both the signal obtained from an arrhythmia signal, i.e. atrial fibrillation other than focal atrial fibrillation, or the signal during sinus rhythm or pacing to develop the template. While in case of P wave or flutter wave isolation it is imperative to use a template based on sinus rhythm or pacing.

An adaptation of the QT interval of the QRST template can take place to correct for differences in heart rate with the arrhythmia signal. One or more fiducial points and windows are identified and annotated for both the QRST template to create a so called annotated QRST template as well as for the arrhythmia signal to create a so called annotated arrhythmia signal. Alignment of the one or more fiducial points and windows annotated in the annotated QRST template and the annotated arrhythmia signal then takes place. After the alignment of the annotated QRST template and annotated arrhythmia signal, the annotated QRST template is resampled and modulated to further compensate for remaining discrepancies in duration and/or voltage. This creates a resampled and modulated QRST template. The atrial activity contained in the arrhythmia signal is isolated by subtracting the resampled and modulated QRST template from the arrhythmia signal. It is important to realize that the QRST template is adaptive to optimize the subtraction by first aligning the QRST template and then resampling and modulating the QRST template. The reason is to account for an arrhythmia discrepancy in heart rate and voltage amplitude of the QRST template with the TU complex of the arrhythmia signal. The present invention includes a variety of techniques that can be used to modulate and resample the QRST template. Generally, this approach of modulation and resampling allows for the surface ECG measurements to retain their intricate spatial and temporal detail within the P wave, fibrillation wave, or flutter wave morphology. The signal processor is capable of unmasking and preserving subtle electrical heart signal details of relatively low-voltage atrial activity signals despite the obscuring superimposed relatively high-voltage QRST complex.

Also in accordance to exemplary embodiments, after the QRST template is effectively subtracted from each measured signal containing an atrial activity of interest, the morphology of the isolated P wave, fibrillation wave or flutter wave can be analyzed in terms of analysis parameters. Examples of analysis parameters are for instance the peak of the wave or the time interval between onset and offset of the wave, or one or more multi-lead integral maps or potential maps of the wave. In an illustrative example an integral map was computed of the isolated P wave. This integral map can be compared with a database of P wave integral maps that was created by for instance pacing. This comparison enables that a particular arrhythmia can be localized from an arrhythmia signal that was obtained by noninvasive techniques. A variety of analysis parameters can be calculated and exchanged with the database. The same type of computation, comparison, or classification can be performed for fibrillation waves and flutter waves with databases containing fibrillation and/or flutter wave analysis parameters.

Finally, the present invention also provides for the application of analyzing and classifying atrial arrhythmias, when atrial depolarization is obscured by the preceding heartbeat's ventricular repolarization.

DETAILED DESCRIPTION

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

Figure 1:
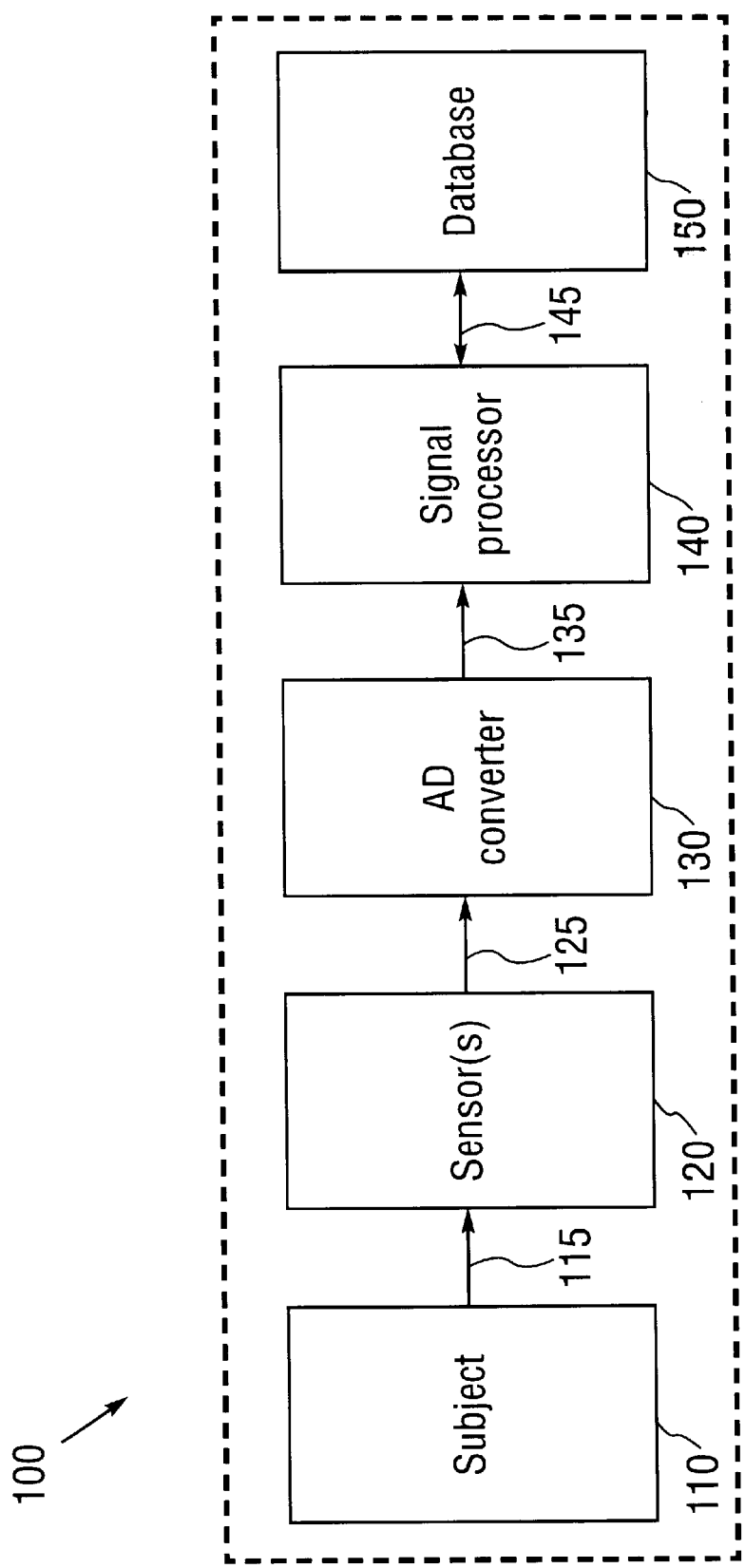
FIG. 1 illustrates an overview of the localization and classification apparatus and method.

To accurately electrocardiographically localize focal triggers during atrial arrhythmias and accessory pathway insertion sites during orthodromic AV reentrant tachycardia and classify atrial fibrillation and atrial flutter, the present invention provides for a noninvasive arrhythmia localization and classification apparatus and method for effectively and optimally separating the atrial activity of interest from a superimposed preceding ventricular activity. An overview of the present invention is shown in FIG. 1 comprising a noninvasive arrhythmia localization and classification apparatus and method 100. The goal of the apparatus and method 100 is to generate an adaptive QRST template that is subtracted from an arrhythmia signal to output an isolated atrial activity in the form of, but not limited to: (1) a P wave in case of focal atrial fibrillation, atrial tachycardia, and orthodromic AV reentrant tachycardia; (2) a fibrillation wave in case of atrial fibrillation other than focal atrial fibrillation; and (3) a flutter wave in case of atrial flutter. The central part of the apparatus and method 100 is a signal processor 140 which will be discussed in more detail below. In general, the signal processor 140 encompasses an adaptation of the QT interval of the QRST template to correct for differences in heart rate with the arrhythmia signal. The signal processor 140 also encompasses a resampling and modulation of the QRST template to correct for discrepancy in heart rate and voltage amplitude of the QRST template with the TU complex of the arrhythmia signal using one or more fiducial points and windows of both the QRST template and the arrhythmia signal. The atrial activity contained in the arrhythmia signal is isolated by subtracting the adapted QRST template from the arrhythmia signal. The signal processor 140 is capable of unmasking and preserving subtle heart signal details of relatively low-voltage atrial activity signals despite the obscuring superimposed relatively high-voltage QRST complex signals.

After the QRST template is effectively subtracted from each arrhythmia signal containing an atrial activity of interest, the morphology of the isolated atrial activity can be analyzed in terms of analysis parameters 145. At least one analysis parameter 145 can be computed. The analysis parameters 145, such as for instance a peak of the wave, duration of the wave or one or more multi-lead integral or potential maps of the wave, can be compared with a database 150 containing a variety of analysis parameters of P waves, fibrillation waves, or flutter waves as shown in FIG. 1. The comparison with database 150 may then lead to a localization and/or classification of a particular arrhythmia using noninvasive techniques upon which treatment guidance or decision making would then be possible. More details on developing a database can be obtained from for instance provisional U.S. application No. 60/189,513 and U.S. non-provisional application No. 09/724,947 filed Nov. 28, 2000 both of which are incorporated herein by reference.

Sensors 120, as shown in FIG. 1, are adapted to detect electrical heart signals 115. The sensors 120 are distributed in an array across the thoracic skin of a subject 110. Generally, this employs a plurality of sensors distributed across the anterior and posterior skin surface of the torso of the subject 110. However, the present invention enables the use of at least one sensor 120. Typically, ten or twenty to forty sensor locations can be chosen. More ideally, sixty-two sensor locations are used on a subject 110. Sensors 120 generally comprise unipolar or bipolar electrodes (passive or active) coupled to the subject's skin, or to an alternative body surface suitable for detecting body surface potentials indicative of the heart's electrical signals 115 (e.g. esophageal recordings). Exemplary arrays for use in locations having large amounts of electromagnetic noise (such as an electrophysiology or catherization lab or other location in which electrosurgery for arrhythmia treatment or electrostimulation of tissues for intracardiac pacing is performed) was described by Metting van Rijn A. C. et al (1993) in *IEEE Trans. Biomed. Eng. BME* 40:302–308. Alternative sensor array structures and associated data acquisition and manipulation components were described by SippensGroenewegen A. et al (1998) in an article entitled "*Body surface mapping during pacing at multiple sites in the human atrium: P wave morphology of ectopic right atrial activation*" published in Circulation 97:369–380, and by Linnenbank A. C. in a 1996 thesis for the University of Amsterdam entitled "*On-site recording, analysis and presentation of multi-channel ECG data*".

As shown in FIG. 1, the electrical heart signals 115 from sensors 120 are preferably acquired simultaneously, amplified and converted into digital signals 135 using an analog-to-digital (AD) converter 130 at a sampling rate of about 500 Hz. Sequential data acquisition from sensors 120 may also be employed. Higher or lower sampling rates are feasible, and ideally a sampling rate of about 1,000 Hz is used. With a lower sampling rate, the data can be upsampled using multirate filter banks or other methods that upsample data such as spline fitting.

The present invention as shown in FIG. 1 includes and is not limited to the transmission of electrical heart signals 115 and digital signals 135 to the signal processor 140 either by conventional electrical cables/wires or by wireless communication. Also the present invention is not limited to combinations of either conventional and wireless communication of the signals. Furthermore, the present invention includes the possibility of both transmission techniques for communication between the signal processor 140 and the database 150. The sensors 120 can also include signal amplification or buffer conversion components as well as wireless transmission components so that remote transmission of digital signals 135 to signal processor 140 will be possible. This can be accomplished by having sensors 120 connected to a box worn by the subject 110, where the amplification and AD conversion occurs such as with ambulatory or Holter ECG recording. In this situation, the signal processor 140 would then also contain the appropriate elements to receive signals through wireless communication. This then enables remote detection, processing, analysis, operation and treatment. For instance, one can think of the scenario that a subject either at a remote location on Earth, at home distanced from a hospital, or even in space who is in need of arrhythmia analysis and treatment for, for instance, atrial tachycardia. The techniques presented in the present invention may then be readily employed (potentially by having the subject wearing the sensors and/or signal recorder) and data of the arrhythmia signals containing information of the atrial tachycardia, represented by the analysis parameters 145, can then be transmitted by wireless communication back to Earth or to a local base station or hospital where tele-operation and/or tele-treatment may be initiated. In addition, the database 150 can be accessed through either conventional data transmission techniques or wireless communication. The scenario can be taken one step further in which the system can also include the possible measures to not only analyze the atrial arrhythmia, but also treat the subject for the arrhythmia.

Figure 2:
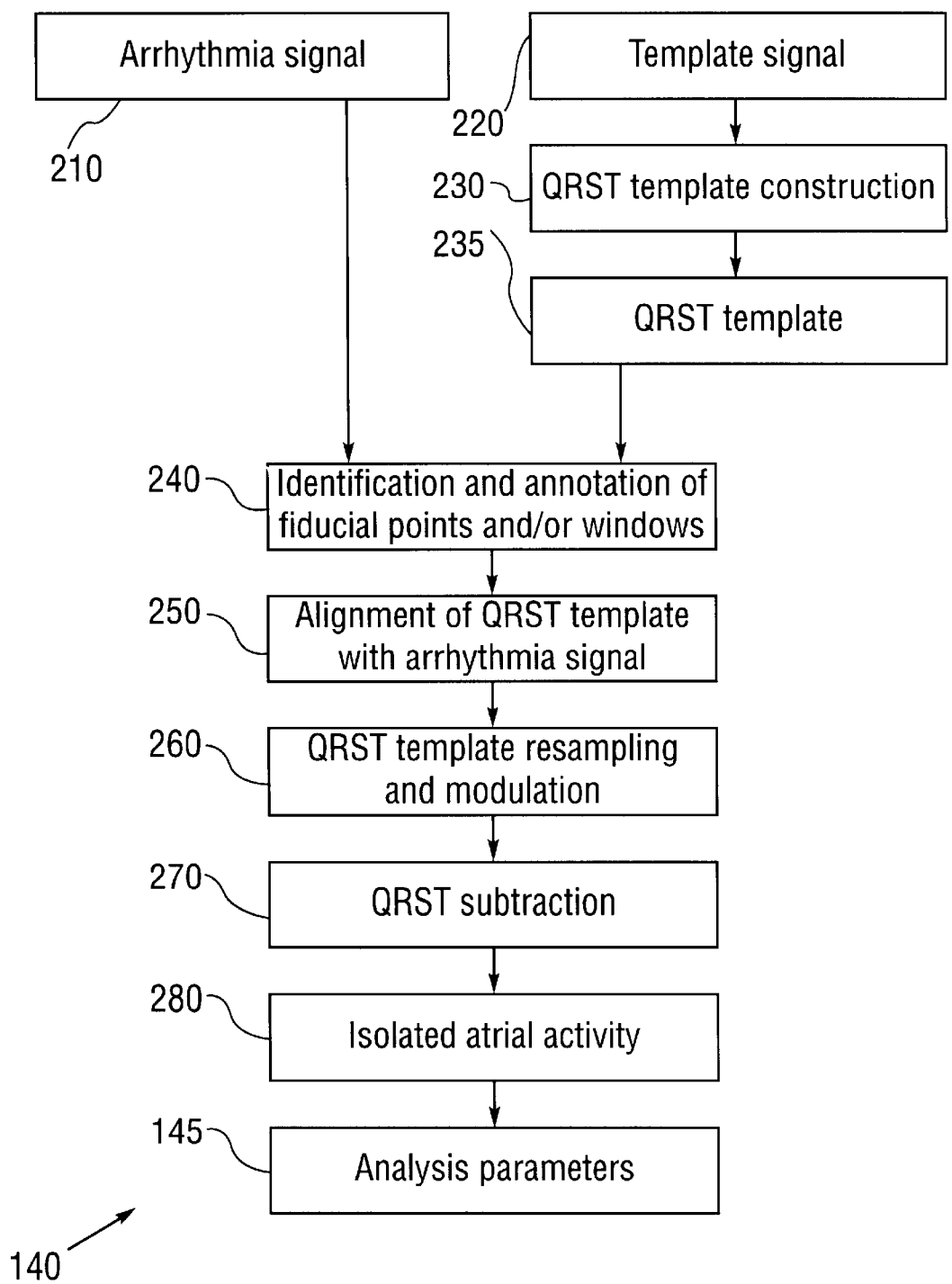
FIG. 2 illustrates an overview of the signal processor.

After the acquisition of the electrical heart signal by the AD converter 130, the signals enter the signal processor 140 as shown in FIG. 1. FIG. 2 shows an exemplary embodiment of the signal processor 140. As shown in FIG. 2, the present invention allows to make a distinction between the electrical heart signal obtained during an arrhythmia, called arrhythmia signal 210, and the electrical heart signal obtained during sinus rhythm or atrial overdrive pacing, called template signal 220, that are used to create the QRST template. It is the arrhythmia signal 210 that is eventually exposed to subtraction of the QRST template, after the template is adapted, to isolate the atrial activity that is obscured from the preceding heartbeat's ventricular activity. As mentioned earlier, the present invention relates to, but is not limited to, the isolation of a P wave, fibrillation wave, or flutter wave. For P wave and flutter wave isolation, the electrical heart signals 115, as shown in FIG. 1, that are eventually used for QRST template construction 230, as shown in FIG. 2, have to be different from the electrical heart signal 115 that is under investigation, i.e. the signal that is recorded during a particular arrhythmia (e.g. focal atrial fibrillation, atrial tachycardia, orthodromic AV reentrant tachycardia, or atrial flutter). However, in case of fibrillation wave analysis, the QRST template may also be designed from the electrical heart signal 115 under investigation, i.e. the signal that is recorded during chronic atrial fibrillation.

Figure 3:
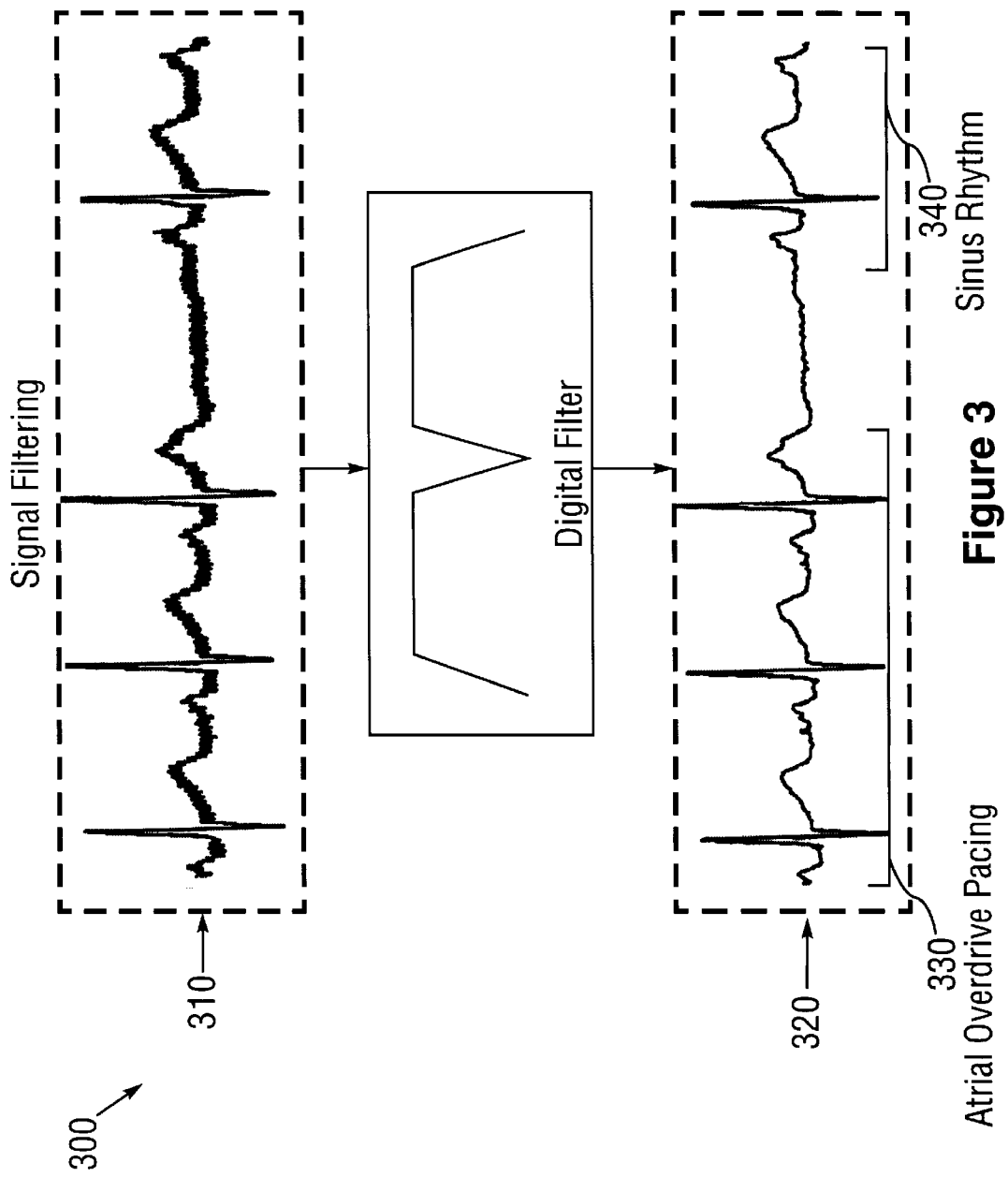
FIG. 3 illustrates the signal filtering according to an embodiment of the present invention.

In an exemplary embodiment, about a hundred cardiac cycles of sixty-two channel ECG data are acquired during sinus rhythm or atrial overdrive pacing for use as template signal 220. Typically, more than ten cycles are used, often more than fifty for the construction 230 of the QRST template 235. Fewer cycles may be used if the spatial and temporal variations of the QRST complexes are relatively low. In general, at least two cardiac cycles of template signals 220 can be used. Digital filtering 300 is applied to both the template signal 220 and arrhythmia signal 210 as shown in FIG. 3, whenever this is decided to be necessary. Digital filtering 300 of the electrical heart signals is usually performed after the signals have been acquired by the AD converter 130, i.e. the analog signals 115 have been converted into digital signals 135, as shown in FIG. 1. Filtering has three different purposes: (1) to correct signals for respiratory related base line drift, (2) to correct signals for high frequency artifacts as is common in data acquisition, and (3) to correct signals for line frequency interference. In the exemplary embodiment, a 0.5 Hz high-pass filter, such as IIR Chebychev Type I filter was used to correct for baseline drift. A 100 Hz low-pass filter, such as a IIR Chebychev Type I filter was used to remove high frequency artifacts. Additionally, a 50–60 Hz notch filter was used to remove line frequency interference. FIG. 3 shows an electrical heart signal before digital filtering indicated by 310 and after filtering indicated by 320. FIG. 3 also shows an example of a digitally filtered signal acquired during atrial overdrive pacing as indicated by 330 and acquired during sinus rhythm illustrated by 340. As one skilled in the art would appreciate, it would also be possible to apply the same filtering to the analog electrical heart signals 115 using analog filtering techniques before acquiring the signals with the AD converter 130, shown in FIG. 1. In addition, the sensors 120, shown in FIG. 1, can also include the filtering components in either analog or digital form.

Figure 4A:
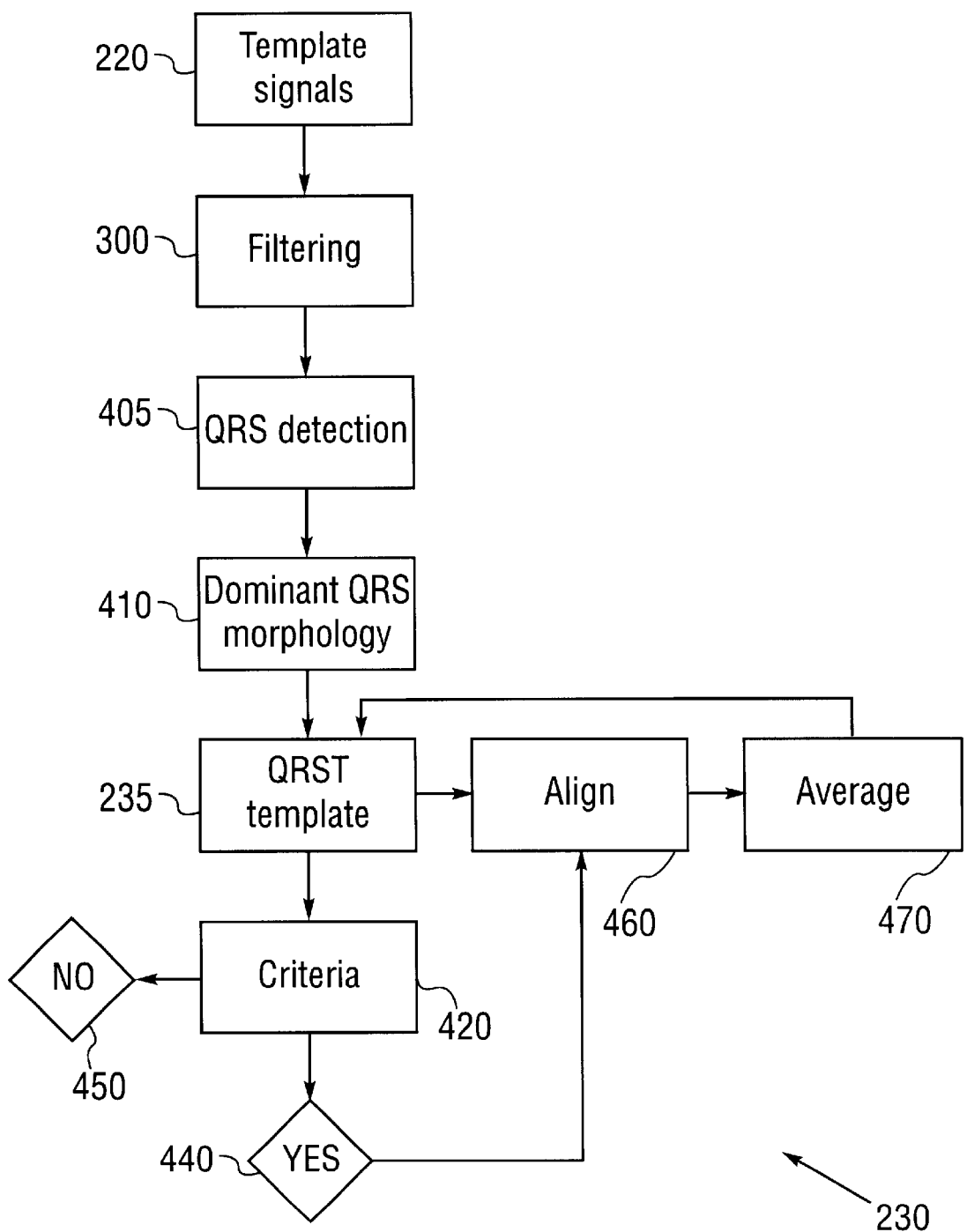
FIG. 4 illustrates the process to construct the QRST template.
Figure 4B:
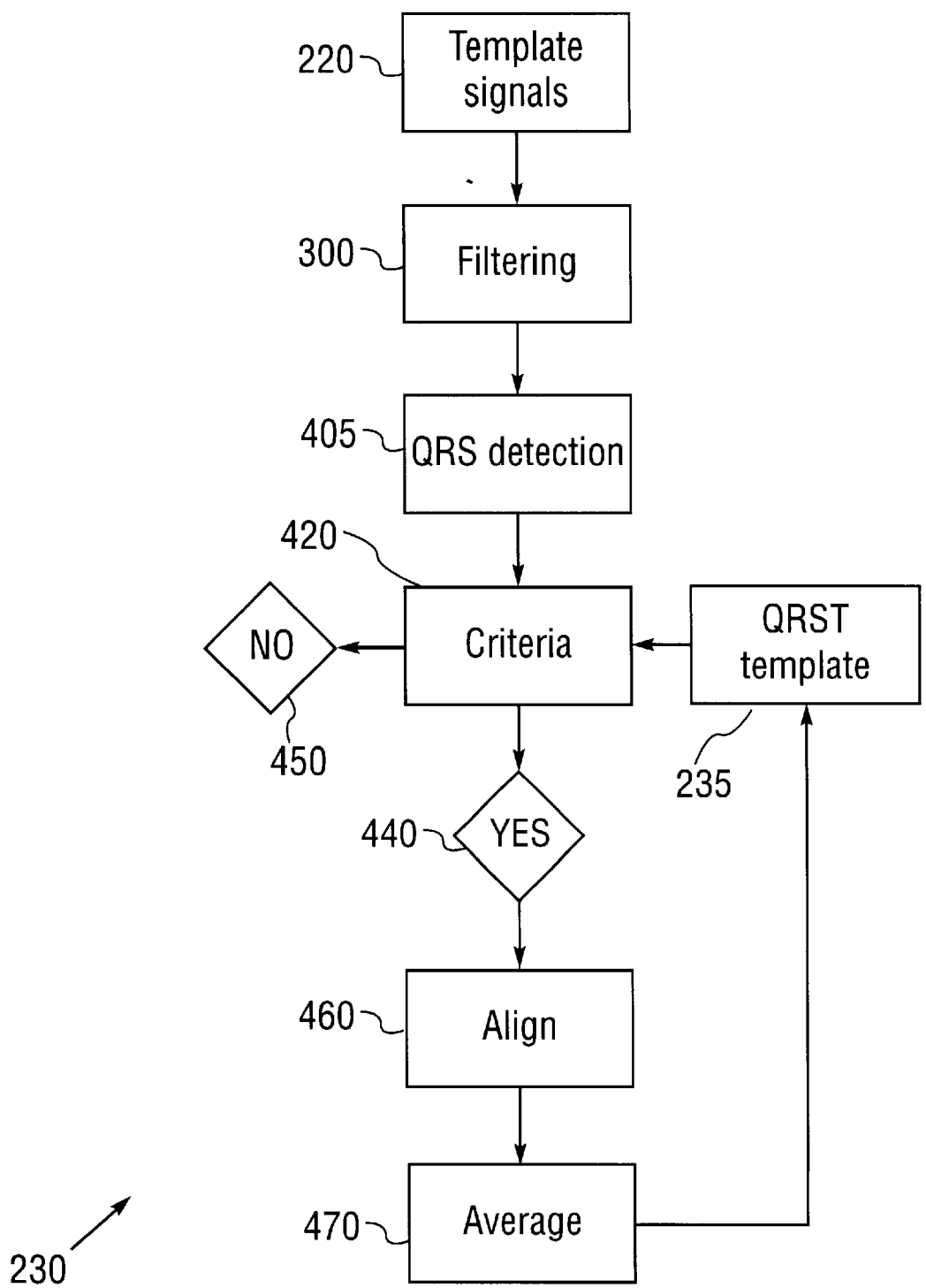

FIG. 4 shows two exemplary embodiments for the construction 230 of a QRST template 235, respectively FIG. 4A and FIG. 4B. FIGS. 4A and 4B are in essence the same except from the initialization process of an initial QRST template 235. FIG. 4B shows the situation when an initial QRST template 235 already exists and which may potentially be further updated and enhanced by adding new template signals 220. FIG. 4A shows the situation when first a dominant QRS morphology 410 needs to be identified and which is then used as a reference to select and add new template signal 220. After filtering, which is performed when decided necessary and indicated by 300, each template signal 220 is analyzed using a complex resonator/comb filter to detect each QRS complex 405 in template signal 220 using a dual-edge threshold detection technique similar to that described by Ruha A. et al (1997), in an article entitled "A real-time microprocessor QRS detector system with a 1-ms timing accuracy for the measurement of ambulatory HRV", published in *IEEE Trans. Biomed. Eng.* 44:159–167, the disclosure of which is incorporated herein by reference. Alternative QRS detection methods may also be used. Subsequently, the dominant QRS morphology 410 is visually identified from the pooled data. Alternative method to identify the dominant QRS morphology 410 might also be used, optionally using automated statistical methods, or the like. It is possible to construct multiple template morphologies, i.e. 2 to 5 based on different dominant QRS morphologies if varying degrees of ventricular aberrancy are present in the arrhythmia signal.

Figure 5:
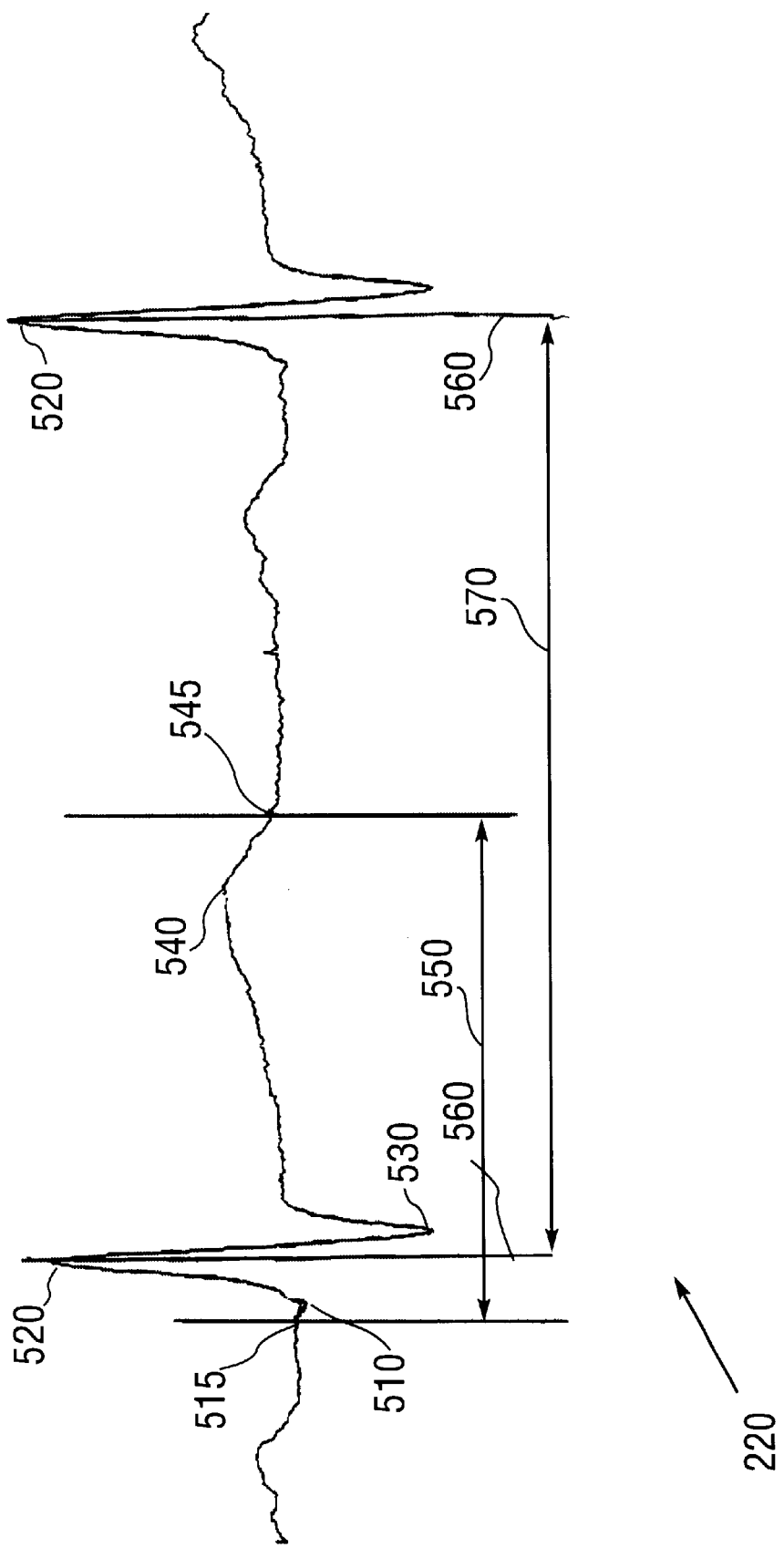
FIG. 5 illustrates the QRS detection according to an embodiment of the present invention with the signal obtained during atrial overdrive pacing.

As mentioned earlier, the dominant QRS morphology 410 in FIG. 4A and the initial QRST template 235 in FIG. 4B are used to identify and select subsequent QRS complexes for QRST template creation from the template signals 220. The identification and selection of subsequent QRS complexes from template signals 220 for QRST template 235 creation is based on one or more criteria 420, for instance: (1) a QRS pattern criteria; and/or (2) a RR interval length criteria. Before these criteria are presented in more detail, it is important to describe and identify markers that can be used in depicting certain time instants and/or windows in these template signals 220. In general, one or more fiducial points and windows can be used as markers. Examples of markers are shown in FIG. 5 based on a template signal 220 obtained during atrial overdrive pacing. In FIG. 5, a peak R wave is indicated by 520 and used to indicate R wave fiducial points 560 and a RR interval is indicated by 570. Also in FIG. 5, a peak of Q wave is indicated by 510, a peak of S wave is indicated by 530, a peak of T wave is indicated by 540, and 550 depicts a QT interval defined as the time interval from the onset of the Q wave 515 and the offset of the T wave 545.

Regarding QRS pattern criteria 420, QRS complexes of each template signal 220 in FIG. 4 are compared with the QRS complex of the QRST template 235 using parametric cross-correlations. In an exemplary embodiment, Pearson's coefficient is computed for a fixed time window sliding over a 20-ms time period. A variety of cross-correlation techniques can be used. The QRST complex of each newly selected QRS complex as shown by 440, for example those selected based on having a Pearson's coefficient that is larger or equivalent to 0.98, is aligned in 460 and averaged in 470 with previously selected QRST complexes from other cycles, and the QRST template 235 is updated. Each QRS complex that does not have an adequate correlation with the QRS complex of the QRST template 235 is excluded as indicated by 450, with these QRS complexes often being ectopic or aberrantly conducted ventricular beats.

Regarding the RR interval length criteria 420, the average RR interval 570, as shown in FIG. 5, is computed after which a minimum RR interval threshold is determined. Only those template signals having an RR interval 570 above the computed threshold are selected, as illustrated by 440, to be aligned in 460 and averaged in 470, as shown in FIG. 4. Other complexes below the threshold are excluded as illustrated by 450.

Figure 6:
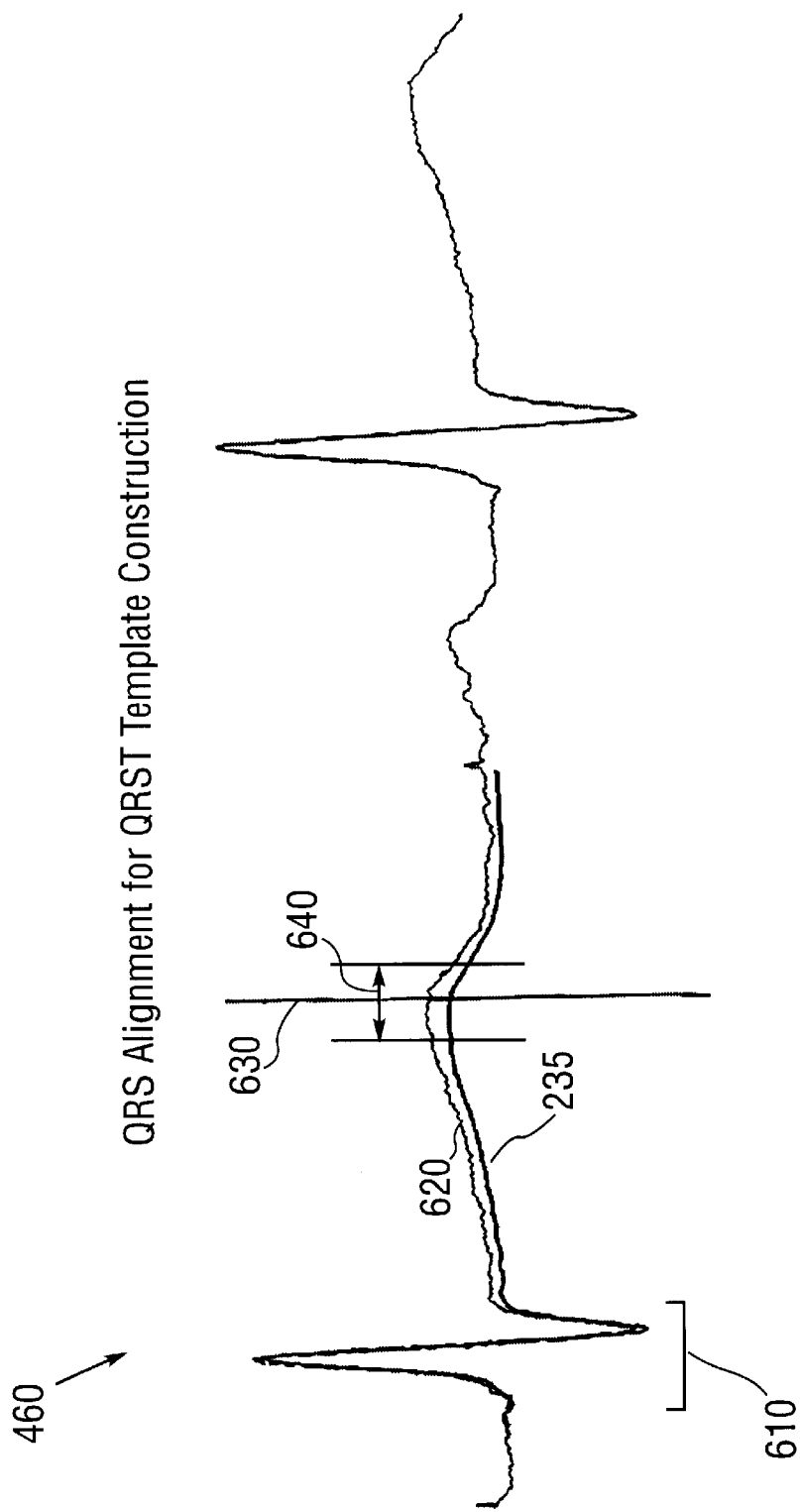
FIG. 6 illustrates the T wave annotation, and a provisional or temporary template that has been aligned with a following QRST complex in the template signal according to an embodiment of the present invention. The signal was obtained during atrial overdrive pacing.
Figure 7:
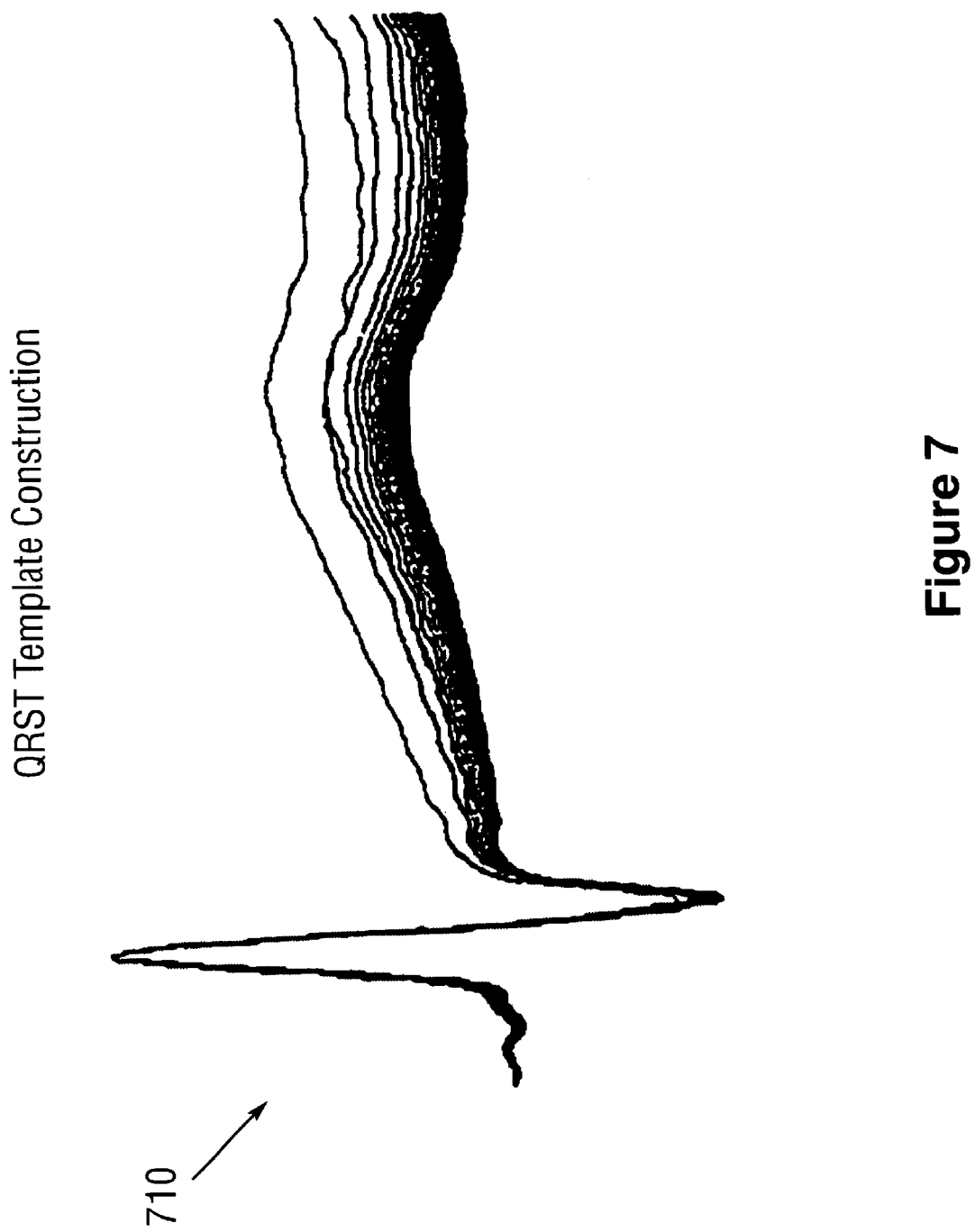
FIG. 7 illustrates the QRST template construction according to an embodiment of the present invention.
Figure 8:
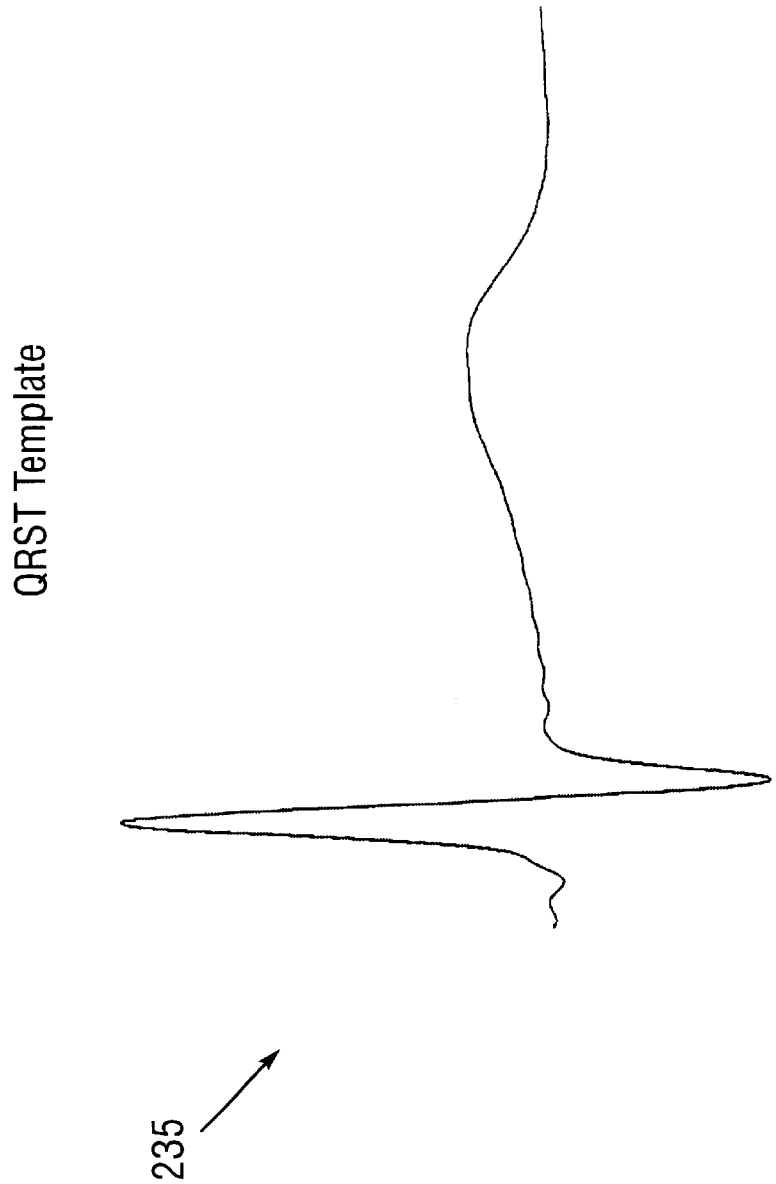
FIG. 8 illustrates the final constructed QRST template developed using averaging of selected complexes according to an embodiment of the present invention.

FIG. 6 shows an exemplary embodiment of the template alignment 460 using template signals obtained during atrial overdrive pacing as discussed in FIG. 4. A selected QRST complex 620 is aligned with QRST template 235. In this particular example, the alignment 460 focuses on aligning the QRS complex 610 of the QRST template 235 with the QRS complex 610 of the selected QRST complex 620. Optionally, to exclude large variability between individual QRST complexes, the alignment 460 can be assisted by a window surrounding the R wave fiducial point. In addition, one can also use T wave fiducial point 630 and/or T wave window 640 annotation to either upsample or down-sample selected QRST complexes to match the QRST template. FIG. 7 shows the situation where subsequently recorded QRST complexes are selected and aligned based on the QRS complex 710. In either case of template construction shown in FIG. 4A or FIG. 4B, an averaged QRST template 235 results as indicated in FIG. 8.

Figure 9:
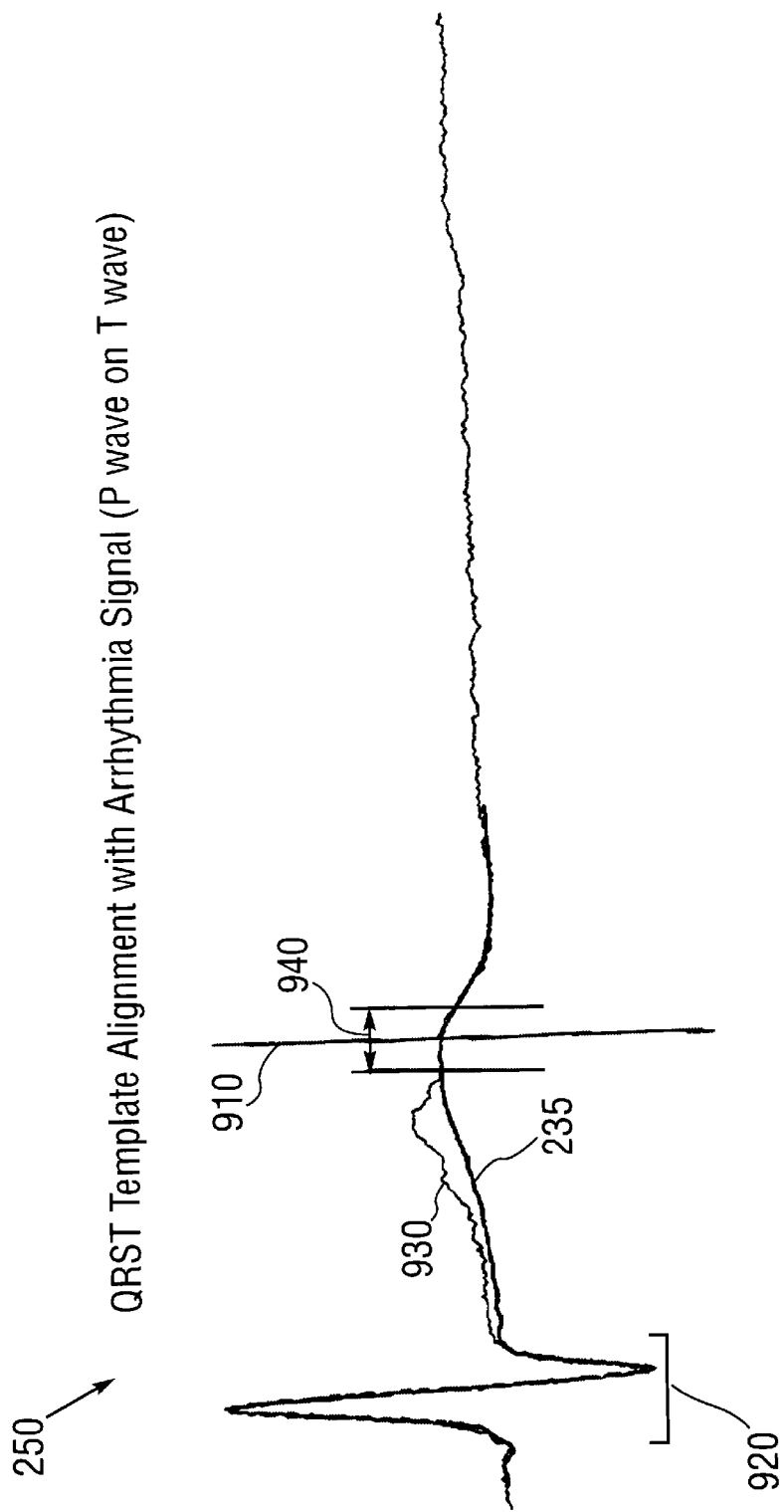
FIG. 9 illustrates the T wave annotation, and a template that has been resampled and aligned with an arrhythmia signal according to an embodiment of the present invention.

As shown in FIG. 2, once the QRST template 235 is constructed in 230, one or more fiducial points and windows are identified and annotated in both the QRST template 235 and the arrhythmia signal 210 as indicated by 240. The identification and annotation is intended to prepare for the subsequent signal alignment of the QRST template 235 and the arrhythmia signal 210 as indicated by 250. The alignment 250 first focuses on aligning one or more fiducial points and/or windows. For instance, in an exemplary embodiment explained below, one can align a QRS pattern and/or T wave annotated by fiducial points and/or windows. In general, one or more fiducial points and windows can be identified and annotated automatically for, for instance, the Q, R, and/or T wave in both the QRST template and the arrhythmia signal. FIG. 5 can be used as a reference of some of these fiducial points and windows. In an exemplary embodiment, FIG. 9 shows the QRST template 235 and an arrhythmia signal 930 containing a P wave of a single ectopic beat or premature atrial contraction superimposed on the T wave. Note that the impulse of this premature atrial contraction blocks in the AV node since there is no subsequent QRST complex to follow. In this exemplary embodiment, the QRS complex 920 is aligned and the T wave fiducial point and window annotated as indicated by 910 and 940, respectively. Typically, a T wave window onset for the QRST template is estimated as 0.64*QT, whereby QT is the time between the Q wave onset 515 and T wave peak offset 545 shown in FIG. 5. The T wave window of the QRST template is adjusted for each QRST complex in the arrhythmia signal based on the QT interval length. Optionally, the operator can (manually or automatically) adjust any fiducial point or window in case of disagreement, such as by manipulating a mouse, joystick, by putting a numerical value, or the like. In any case, the template's QRS fiducial points or windows and T wave fiducial points or windows are aligned with the respective windows of the arrhythmia signal creating an aligned QRST template.

As shown in FIG. 2, after the alignment 250, the aligned QRST template 235 is resampled as well as amplitude modulated as indicated by 260 with respect to the arrhythmia signal. The QRST template resampling and modulation is performed to compensate for remaining one or more discrepancies of the QRST template with the arrhythmia signal, as a result of rate-related differences in the QRST interval, and voltage amplitude, as a consequence of variations in peak R and T wave voltage which may be caused by e.g. respiratory variation. The resampling and modulation is essential for obtaining optimal subtraction performance of the TU wave complex. Optionally, cubic spline interpolation methods may be used for template resampling, although other multi-rate processing methods can also be used. Together with these adjusting techniques, the present invention also includes various means for adjusting the fiducial points and windows referred to as signal sliding means, signal stretching or compressing means, variable signal adjusting means, or the like. The general idea in the sliding, stretching or compressing, and variable adjusting means is that one or more fiducial points and/or windows in the QRST template can be adjusted either in horizontal or vertical direction, by sliding, or stretching or compressing the QRST template over the arrhythmia signal, or adjusting the QRST template by a variable amount over the arrhythmia signal. For example, alignment of the arrhythmia signal and the QRST template may be performed manually, or automatically by sliding windows over each other in 10-ms increments and calculating cross-correlation coefficients. Another example is that a variable is chosen that is for instance added to, subtracted from, or multiplied with the QRST template to align with the arrhythmia signal.

Figure 10:
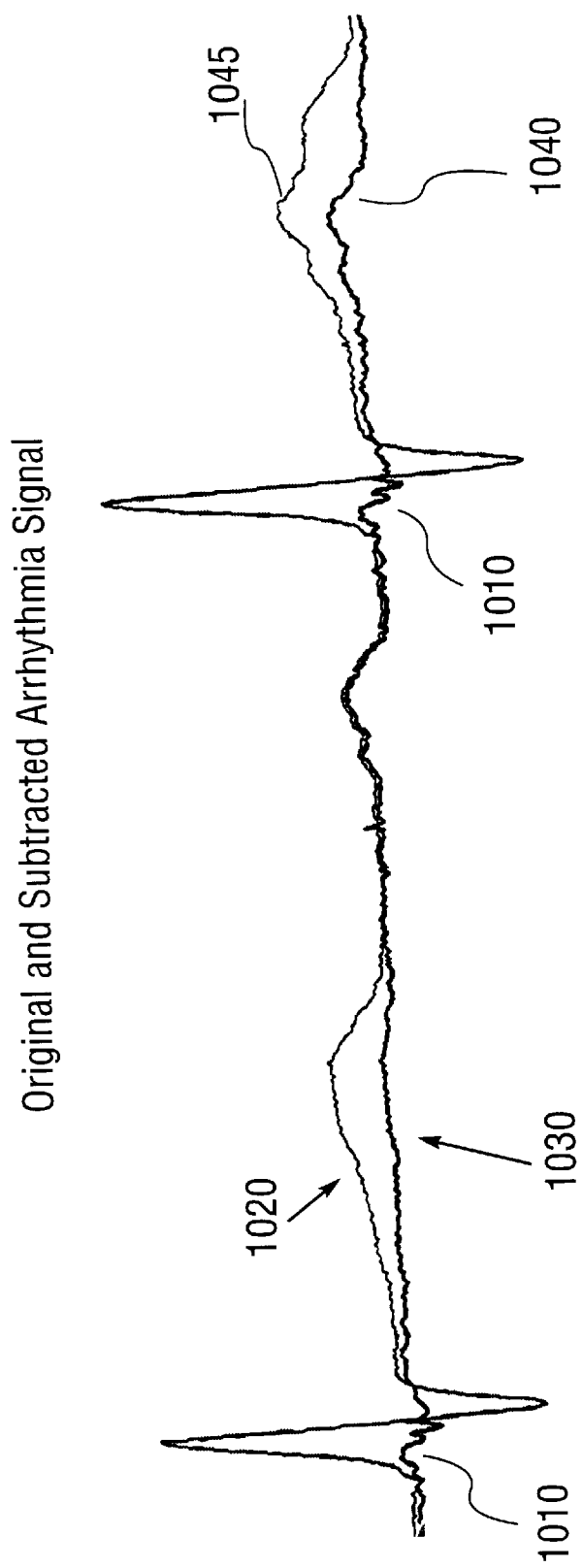
FIG. 10 illustrates the arrhythmia signal before and after subtraction of the QRST template according to an embodiment of the present invention. The arrhythmia signal was artificially created by atrial overdrive pacing and introducing an early atrial extrastimulus to generate a P wave superimposed on a T wave.
Figure 11:
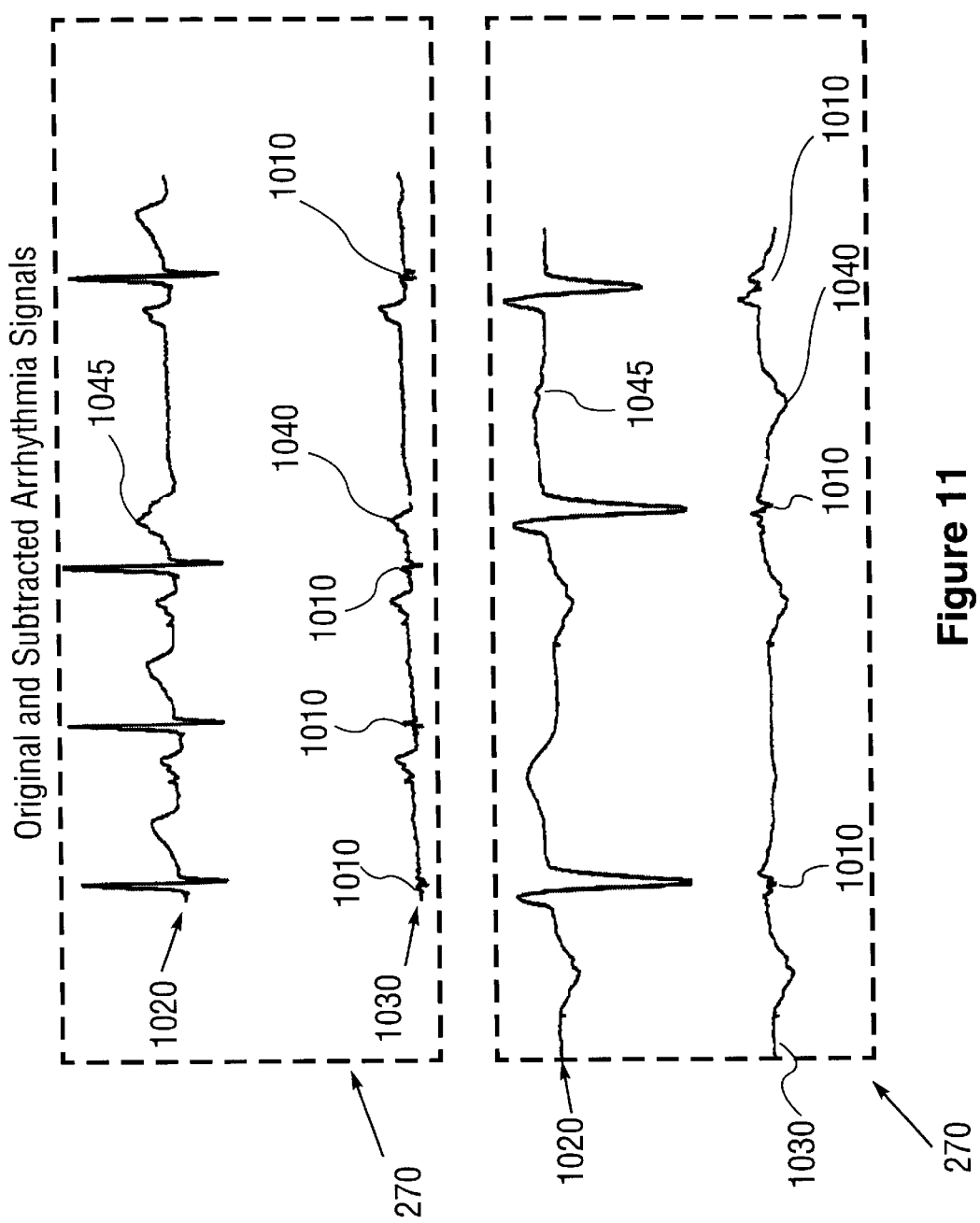
FIG. 11 illustrates the arrhythmia signal before and after subtraction of the QRST template wherein P wave on T wave are annotated according to an embodiment of the present invention. The arrhythmia signal was artificially created by atrial overdrive pacing and introducing an early atrial extrastimulus to generate a P wave superimposed on a T wave.

As shown in FIG. 2, the resampled and modulated QRST template is subtracted from the arrhythmia signal as indicated by 270. The subtraction 270 can be better understood from FIGS. 10 and 11 in which exemplary embodiments are shown. FIGS. 10 and 11 show an artificial arrhythmia signal 1020 created by atrial overdrive pacing and introducing an early atrial extrastimulus to generate a P wave superimposed on the T wave and a resulting subtracted arrhythmia signal 1030. In the exemplary embodiments of FIGS. 10 and 11, an isolated P wave 1040 is obtained by subtraction of the QRST template from the arrhythmia signal 1020 that contained a P wave on a T wave as indicated by 1045. The subtraction 270, as shown in FIG. 2, is performed channel-to-channel according to the position of sensor 120 shown in FIG. 1. Additional low-pass filtering can be carried out to minimize or smooth possible QRS leakage 1010 after the QRST template subtraction. The remaining electrical signal after QRST subtraction features a P wave which was effectively isolated from the previously superimposed TU wave or obscuring preceding ventricular repolarization.

Figure 12:
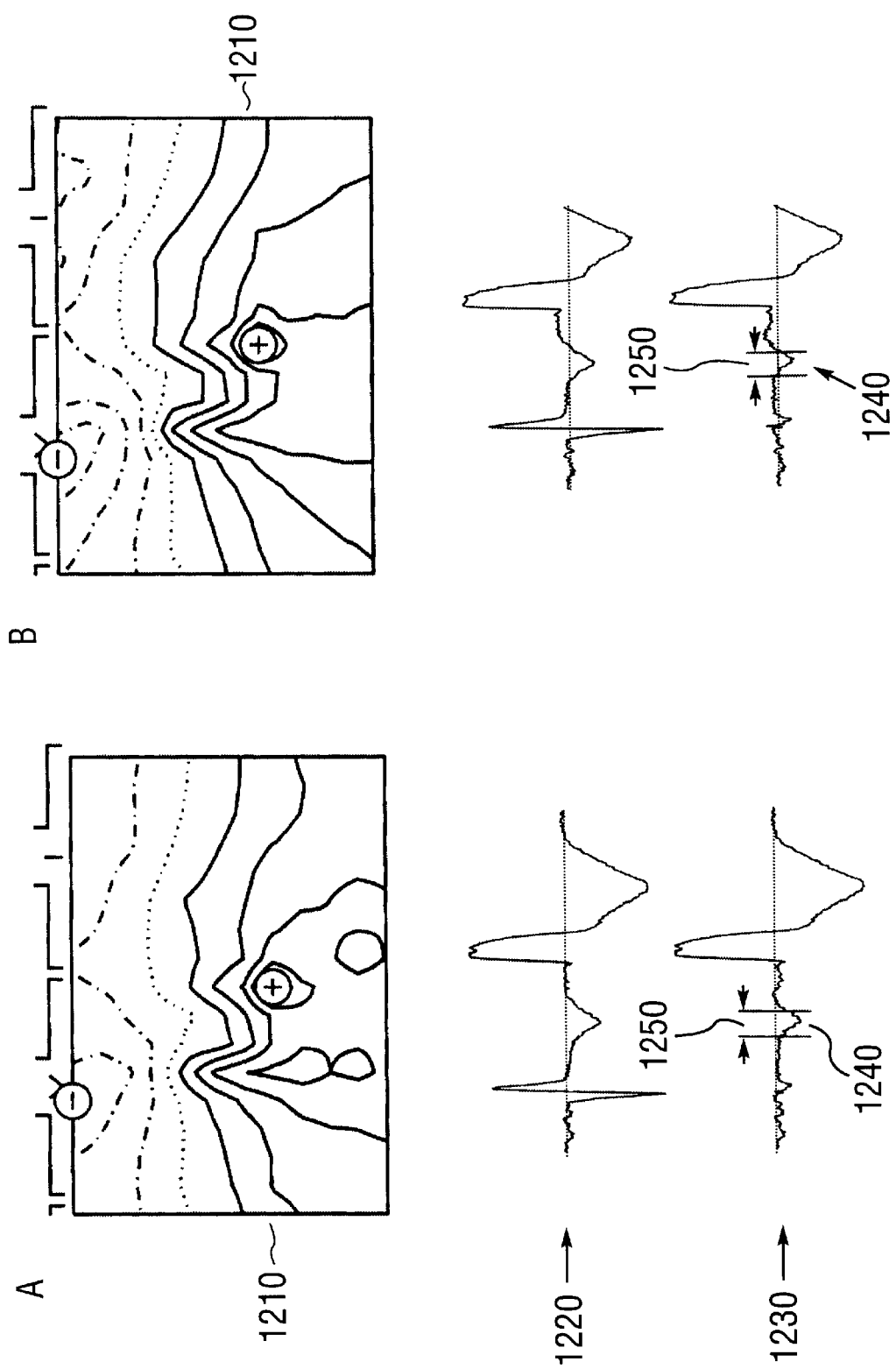
FIG. 12 graphically illustrates the method for calculating an integral value across a selected time portion of a heart signal cycle from multiple sensors of an isolated P wave according to an embodiment of the present invention.

After the QRST template is effectively subtracted from each measured signal containing for instance a P wave (alternatively a fibrillation or flutter wave) of interest, the morphology of the isolated P wave can be analyzed in terms of one or more analysis parameters 145 as shown in FIGS. 1 and 2. Examples of analysis parameters 145 are for instance a P wave integral or potential map, a peak of the P wave, or a time interval between onset and offset of the P wave. FIG. 12 shows two illustrative examples in which a P wave integral value is computed across a selected time portion 1250 of an electrical heart signal from multiple sensors of an isolated P wave 1240 of an ectopic atrial beat or premature atrial contraction. The electrical heart signals used in this particular example show a scalar ECG tracing that was acquired at one of the 62 sensor positions used in this recording. In FIG. 12, 1220 shows the original arrhythmia signal while 1230 shows the subtracted signal with the isolated P wave. Note that the second QRST complex in both examples shows major QRST leakage due to ventricular aberrancy and consequent mismatch with the QRST template. A P wave integral map 1210 is constructed using integral values from isolated P waves obtained by these multiple sensors. FIG. 12 also shows that the two isolated P waves (Panels A and B) contain the same atrial ectopic beat morphology although they were obtained in different arrhythmia signals. As shown in FIG. 1, these P wave integral maps 1210 can then be compared with the database 150 that contains a variety of P wave analysis parameters 145 that were previously created by for instance pacing. The comparison of analysis parameters 145 enables that a particular atrial arrhythmia can be localized or classified using an arrhythmia signal that was obtained by noninvasive electrocardiographic techniques. The same type of computation, comparison, or classification as described for P waves can also be performed for fibrillation waves (e.g. at least one fibrillation wave), flutter waves, or any other isolated atrial activity wave. In addition, classification and comparison using a database is just one way, and the invention is not limited to other techniques of classification and comparison, including visual or manual comparison and classification.

It is important to note that while the present invention has been described in the context of a fully functional signal analysis and processing system, those skilled in the art will appreciate that the mechanism of the present invention is capable of being distributed and communicated in the form of a computer readable medium of instructions in a variety of forms, and that the present invention applies equally regardless of the particular type of signal bearing and transmission media used to actually carry out the distribution and communication. Examples of computer readable medium include recordable type media such as floppy disks, tape, optical disks, CD-ROMs. Transmission type media contain analog and digital communication links including wireless communication and Internet-based data exchange and communication.

It will be clear to one skilled in the art that the above embodiment may be altered in many ways without departing from the scope of the invention. Accordingly, the scope of the invention should be determined by the following claims and their legal equivalents.

What is claimed is:

1. A noninvasive arrhythmia localization and classification apparatus, comprising a signal processor which is adapted to receive electrical heart signals indicative of a heart's atrial and ventricular activity wherein said signal analyzer is further adapted to:
   (a) receive an arrhythmia signal that contains said electrical heart signals obtained during an arrhythmia and said atrial activity is obscured by said ventricular activity;
   (b) receive at least two template signals to construct a QRST template;
   (c) identify and annotate one or more fiducial points and windows of said arrhythmia signal to create an annotated arrhythmia signal;
   (d) identify and annotate one or more fiducial points and windows of said QRST template to create an annotated QRST template;
   (e) align said annotated QRST template with said annotated arrhythmia signal using said one or more fiducial points and windows and thereby creating an aligned QRST template;
   (f) resample and modulate said aligned QRST template to compensate for on one or more discrepancies between said aligned QRST template and said annotated arrhythmia signal using said one or more fiducial points and windows and thereby creating a resampled and modulated QRST template; and
   (g) isolate said atrial activity from said arrhythmia signal obtained by a subtraction of said resampled and modulated QRST template from said arrhythmia signal.

2. The apparatus as set forth in claim 1, wherein said at least two template signals are obtained during a sinus rhythm.

3. The apparatus as set forth in claim 1, wherein said at least two template signals are obtained during an atrial overdrive pacing.

4. The apparatus as set forth in claim 1, wherein said at least two template signals are obtained during said arrhythmia and said arrhythmia signal is obtained during atrial fibrillation.

5. The apparatus as set forth in claim 1, further comprising at least one sensor which is adapted to detect said electrical heart signals and to transmit said electrical heart signals to said signal processor.

6. The apparatus as set forth in claim 1, wherein said at least one sensor is adapted to be placed on a suitable body surface of a subject.

7. The apparatus as set forth in claim 1, further comprising an analog-to-digital converter which is adapted to convert said electrical heart signals into digital signals.

8. The apparatus as set forth in claim 1, wherein said signal processor is adapted to annotate one or more fiducial points and windows of a QRS complex of said QRST template.

9. The apparatus as set forth in claim 1, wherein said signal processor is adapted to annotate one or more fiducial points and windows for a T wave of said QRST template.

10. The apparatus as set forth in claim 1, wherein said signal processor is adapted to annotate one or more fiducial points and windows of a QRS complex of said arrhythmia signal.

11. The apparatus as set forth in claim 1, wherein said signal processor is adapted to annotate one or more fiducial points and windows for a T wave of said arrhythmia signal.

12. The apparatus as set forth in claim 1, wherein said signal processor is adapted to apply filtering to eliminate possible QRS leakage after said subtraction.

13. The apparatus as set forth in claim 1, wherein said signal processor is adapted to apply filtering of said electrical heart signals.

14. The apparatus as set forth in claim 13, wherein said signal processor is adapted to apply a high-pass frequency filter to remove baseline drift.

15. The apparatus as set forth in claim 13, wherein said signal processor is adapted to apply a low-pass frequency filter to remove high frequency artifacts.

16. The apparatus as set forth in claim 13, wherein said signal processor is adapted to apply a notch filter to remove line frequency interference.

17. The apparatus as set forth in claim 1, wherein said signal processor is adapted to resample and modulate said QRST template for a TU complex discrepancy in a rate and at least one amplitude compared to said arrhythmia signal to create said resampled and modulated QRST template.

18. The apparatus as set forth in claim 17, wherein said signal processor is adapted to adjust said fiducial points and windows using signal sliding means to resample and modulate said QRST template.

19. The apparatus as set forth in claim 17, wherein said signal processor is adapted to adjust said fiducial points and windows using signal stretching or compressing means to resample and modulate said QRST template.

20. The apparatus as set forth in claim 17, wherein said signal processor is adapted to adjust said fiducial points and windows using variable signal adjusting means to resample and modulate said QRST template.

21. The apparatus as set forth in claim 1, wherein said signal processor is adapted to compute at least one analysis parameter of said atrial activity from said isolated atrial activity of said arrhythmia signal.

22. The apparatus as set forth in claim 21, wherein said signal processor is adapted to determine a localization or classification of said arrhythmia by a comparison of said at least one analysis parameter of said isolated atrial activity with a database containing said analysis parameters of said isolated atrial activity.

23. The apparatus as set forth in claim 21, wherein said arrhythmia signal is selected from the group focal atrial fibrillation, atrial tachycardia and orthodromic atrioventricular reentrant tachycardia and said isolated atrial activity is a P wave.

24. The apparatus as set forth in claim 23, wherein said signal processor is adapted to determine a localization of said arrhythmia by a comparison of said at least one analysis parameter of said isolated P wave with a database containing said analysis parameters of said P wave.

25. The apparatus as set forth in claim 21, wherein said arrhythmia is an atrial fibrillation and said isolated atrial activity is at least one fibrillation wave.

26. The apparatus as set forth in claim 25, wherein said signal processor is adapted to determine a classification of said arrhythmia by a comparison of said analysis parameter of said at least one isolated fibrillation wave with a database containing said analysis parameters of said fibrillation wave.

27. The apparatus as set forth in claim 21, wherein said arrhythmia is atrial flutter and said isolated atrial activity is a flutter wave.

28. The apparatus as set forth in claim 27, wherein said signal processor is adapted to determine a classification of said arrhythmia by a comparison of said analysis parameter of said isolated flutter wave with a database containing said analysis parameters of said flutter wave.

29. The apparatus as set forth in claim 1, wherein said signal processor is adapted to select at least two QRST complexes from said at least two template signals to create said QRST template.

30. The apparatus as set forth in claim 29, wherein said signal processor is adapted to compute an average of said selected QRST complexes by averaging their QRST intervals to create said QRST template.

31. The apparatus as set forth in claim 29, wherein said signal processor is adapted to detect a QRS complex in each said QRST complex.

32. The apparatus as set forth in claim 31, wherein said signal processor is adapted to select at least one dominant QRS morphology.

33. The apparatus as set forth in claim 32, wherein said signal processor is adapted to add at least one said QRST complex to said QRST complex with said at least one dominant QRS morphology based on at least one criteria.

34. The apparatus as set forth in claim 33, wherein said criteria is a QRS pattern.

35. The apparatus as set forth in claim 33, wherein said criteria is a RR interval length.

36. The apparatus as set forth in claim 35, wherein said signal processor is adapted to mark one or more fiducial points and windows to determine said RR interval length of selected said QRST complexes to create said QRST template.

37. The apparatus as set forth in claim 35, wherein said signal processor is adapted to compute an average of said RR interval length of said selected QRST complexes to create said QRST template.

38. A method for noninvasive arrhythmia localization and classification, comprising the steps of:
(a) providing a signal processor for receiving electrical heart signals indicating a heart's atrial and ventricular activity;
(b) receiving at least two template signals for constructing a QRST template;
(c) receiving an arrhythmia signal containing said electrical heart signals obtained during an arrhythmia and said atrial activity is obscured by said ventricular activity;
(d) identifying and annotating one or more fiducial points and windows of said QRST template and creating an annotated QRST template;
(e) identifying and annotating one or more fiducial points and windows of said arrhythmia signal and creating an annotated arrhythmia signal;
(f) aligning said annotated QRST template to said annotated arrhythmia signal using said one or more fiducial points and windows and thereby creating an aligned QRST template;
(g) resampling and modulating said aligned QRST template to compensate for on one or more discrepancies between aligned QRST template and said annotated arrhythmia signal using said one or more fiducial points and windows and thereby creating a resampled and modulated QRST template; and
(h) isolating said atrial activity from said arrhythmia signal obtained by subtracting said resampled and modulated QRST template from said arrhythmia signal.

39. The method as set forth in claim 38, wherein said at least two template signals for constructing a QRST template are obtained during a sinus rhythm.

40. The method as set forth in claim 38, wherein said at least two template signals for constructing a QRST template are obtained during an atrial overdrive pacing.

41. The method as set forth in claim 38, wherein said at least two template signals for constructing a QRST template are obtained during said arrhythmia and said arrhythmia signal is obtained during an atrial fibrillation.

42. The method as set forth in claim 38, further comprising the step of providing at least one sensor for detecting said electrical heart signals and transmitting said electrical heart signals to said signal processor.

43. The method as set forth in claim 38, wherein said step of providing at least one sensor further comprises the step of placing said at least one sensor on a suitable body surface of a subject.

44. The method as set forth in claim 38, further comprising the step of providing an analog-to-digital converter for converting said electrical heart signals into digital signals.

45. The method as set forth in claim 38, wherein said step of identifying and annotating one or more fiducial points and windows of said QRST template further comprises the step of identifying one or more fiducial points and windows of a QRS complex of said QRST template.

46. The method as set forth in claim 38, wherein said step of identifying and annotating one or more fiducial points and windows of said QRST template further comprises the step of identifying one or more fiducial points and windows of a T wave of said QRST template.

47. The method as set forth in claim 38, wherein said step of identifying and annotating one or more fiducial points and windows of said arrhythmia signal further comprises the step of identifying one or more fiducial points and windows of a QRS complex of said arrhythmia signal.

48. The method as set forth in claim 38, wherein said step of identifying and annotating one or more fiducial points and windows of said arrhythmia signal further comprises the step of identifying one or more fiducial points and windows of a T wave of said arrhythmia signal.

49. The method as set forth in claim 38, further comprises the step of applying filtering to eliminate possible QRS leakage after said step of subtracting.

50. The method as set forth in claim 38, further comprising the step of applying filtering to said electrical heart signals.

51. The method as set forth in claim 50, wherein said step of applying filtering further comprises the step of applying high-pass frequency filtering to remove baseline drift.

52. The method as set forth in claim 50, wherein said step of applying filtering further comprises the step of applying low-pass frequency filtering to remove high frequency artifacts.

53. The method as set forth in claim 50, wherein said step of applying filtering further comprises the step of applying notch filtering to remove line frequency interference.

54. The method as set forth in claim 38, wherein said step of resampling and modulating said annotated QRST template further comprises the step of resampling and modulating said QRST template for a TU complex discrepancy in a rate and at least one amplitude compared to said arrhythmia thereby creating said resampled and modulated QRST template.

55. The method as set forth in claim 54, wherein signal processor is adapted to adjust said fiducial points and windows using signal sliding means to resample and modulate said QRST template.

56. The method as set forth in claim 54, wherein signal processor is adapted to adjust said fiducial points and windows using signal stretching means to resample and modulate said QRST template.

57. The method as set forth in claim 54, wherein signal processor is adapted to adjust said fiducial points and windows using variable signal adjusting means to resample and modulate said QRST template.

58. The method as set forth in claim 38, further comprises the step of computing at least one analysis parameter of said atrial activity from said isolated atrial activity of said arrhythmia signal.

59. The method as set forth in claim 58, further comprises the step of determining a localization or classification of said arrhythmia by comparing of said at least one analysis parameter of said isolated atrial activity with a database containing said analysis parameters of said isolated atrial activity.

60. The method as set forth in claim 58, wherein said arrhythmia signal is selected from the group focal atrial fibrillation, atrial tachycardia, and orthodromic atrioventricular reentrant tachycardia and said isolated atrial activity is a P wave.

61. The method as set forth in claim 60, further comprises the step of determining a localization of said arrhythmia by comparing of said at least one analysis parameter of said isolated P wave with a database containing said analysis parameters of said P wave.

62. The method as set forth in claim 58, wherein said arrhythmia signal is an atrial fibrillation and said isolated atrial activity is at least one fibrillation wave.

63. The method as set forth in claim 62, further comprises the step of determining a classification of said arrhythmia by comparing of said at least one analysis parameter of said at least one isolated fibrillation wave with a database containing said analysis parameters of said fibrillation wave.

64. The method as set forth in claim 58, wherein said arrhythmia signal is an atrial flutter and said isolated atrial activity is a flutter wave.

65. The method as set forth in claim 64, further comprises the step of determining a classification of said arrhythmia by comparing of said at least one analysis parameter of said isolated flutter wave with a database containing said analysis parameters of said flutter wave.

66. The method as set forth in claim 38, wherein said step of constructing a QRST template further comprises the step of selecting at least two QRST complexes for creating said QRST template.

67. The method as set forth in claim 66, wherein said step of selecting at least two QRST complexes further comprises the step of detecting a QRS complex in each said QRST complex.

68. The method as set forth in claim 67, wherein said step of constructing a QRST template further comprises the step of computing an average of said selected QRST complexes by averaging their QRST intervals for creating said QRST template.

69. The method as set forth in claim 67, wherein said step of detecting a QRS complex further comprises the step of selecting at least one dominant QRS morphology.

70. The method as set forth in claim 69, wherein said step of constructing a QRST template further comprises the step of adding said at least one QRST complex to said QRST complex with said at least one dominant QRS morphology based on at least one criteria.

71. The method as set forth in claim 70, wherein said step of adding said at least one QRST complex based on at least one criteria further comprises the step of comparing a QRS pattern and said QRS pattern is said at least one criteria.

72. The method as set forth in claim 70, wherein said step of selecting said at least one QRST complex using at least one criteria further comprises the step of comparing a RR interval length and said RR interval length is said at least one criteria.

73. The method as set forth in claim 72, wherein said step of determining a RR interval length further comprises the step of marking R wave fiducial points for determining said RR interval length of each said selected QRST complex for creating said QRST template.

74. The method as set forth in claim 73, wherein said step of using a RR interval length further comprises the step of computing an average of said RR interval length of each said selected QRST complex for creating said QRST template.

\* \* \* \* \*